(12) United States Patent
Reimer et al.

(10) Patent No.: US 9,025,244 B2
(45) Date of Patent: May 5, 2015

(54) ILLUMINATING SYSTEM AND AN OPTICAL VIEWING APPARATUS INCORPORATING SAID ILLUMINATING SYSTEM

(75) Inventors: Peter Reimer, Ellwangen (DE); Markus Bausewein, Aalen (DE); Helge Jess, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 249 days.

(21) Appl. No.: 12/801,526

(22) Filed: Jun. 14, 2010

(65) Prior Publication Data

US 2010/0321772 A1 Dec. 23, 2010

(30) Foreign Application Priority Data

Jun. 17, 2009 (DE) .......................... 10 2009 025 127

(51) Int. Cl.
*G02B 21/06* (2006.01)
*G02B 21/00* (2006.01)
*A61B 5/00* (2006.01)
*A61B 1/04* (2006.01)
(Continued)

(52) U.S. Cl.
CPC .......... *A61B 5/0071* (2013.01); *G02B 21/0032* (2013.01); *A61B 1/043* (2013.01); *A61B 1/0638* (2013.01); *A61B 1/0669* (2013.01); *A61B 1/0684* (2013.01); *A61B 5/0084* (2013.01); *A61B 19/5223* (2013.01); *G01N 21/6458* (2013.01); *G02B 21/0012* (2013.01); *G02B 21/06* (2013.01); *G02B 23/2461* (2013.01); *A61B 1/063* (2013.01); *A61B 1/0646* (2013.01)

(58) Field of Classification Search
CPC ............... G02B 21/00; G02B 21/0012; G02B 21/0028; G02B 21/0032; G02B 21/0076; G02B 21/06; G02B 21/16

USPC .................. 359/618, 634, 368–390, 885–892
See application file for complete search history.

(56) References Cited

U.S. PATENT DOCUMENTS 5,748,367 A * 5/1998 Lucke et al. .................. 359/385
5,838,491 A * 11/1998 Gartner et al. ................ 359/385
(Continued)

FOREIGN PATENT DOCUMENTS

DE 20 2004 010 121 8/2004
DE 20 2006 000 018 3/2006
EP 2 015 124 1/2009

OTHER PUBLICATIONS

English translation of the Office action of the German Patent Office dated Feb. 26, 2010 in German patent application 10 2009 025 127.8 on which the claim of priority is based.

*Primary Examiner* — Thong Nguyen
(74) *Attorney, Agent, or Firm* — Walter Ottesen P.A.

(57) ABSTRACT

An illuminating system (21) is provided for an optical viewing apparatus (1) which can be operated in a fluorescence mode. The illuminating system includes at least one broadband light source (31) for illuminating a viewed object (3) and at least one narrowband light source (37) for exciting fluorescence in the viewed object (3) and/or for background illumination in the fluorescence mode. The illuminating system further includes a light conductor (23) having a light source end inlet end (49) and an outlet end (25) facing toward the viewed object. Furthermore, the illuminating system (21, 210) includes a superposer (43) for superposing the light of the narrowband light source (37) with the light of the broadband light source (31). The superposer (43) is mounted at the inlet end (49) or at the light source side ahead of the inlet end (49) of the light conductor (23).

11 Claims, 7 Drawing Sheets

(51) Int. Cl.
*A61B 1/06* (2006.01)
*A61B 19/00* (2006.01)
*G01N 21/64* (2006.01)
*G02B 23/24* (2006.01)

(56) References Cited

U.S. PATENT DOCUMENTS

| | | | |
|---|---|---|---|
| 6,134,365 A * | 10/2000 | Colvin | 385/116 |
| 6,510,338 B1 | 1/2003 | Irion et al. | |
| 7,206,128 B2 * | 4/2007 | Tonooka | 359/388 |
| 7,215,468 B2 * | 5/2007 | Nakata | 359/386 |
| 2005/0111090 A1 | 5/2005 | Kleinteich et al. | |
| 2005/0152029 A1 | 7/2005 | Endo | |
| 2005/0224692 A1 | 10/2005 | Tsuchiya et al. | |
| 2006/0232855 A1 | 10/2006 | Nakamura et al. | |
| 2008/0106787 A1 * | 5/2008 | Tsutsui et al. | 359/385 |
| 2008/0180640 A1 * | 7/2008 | Ito | 353/31 |
| 2008/0198448 A1 | 8/2008 | Ganser et al. | |

* cited by examiner

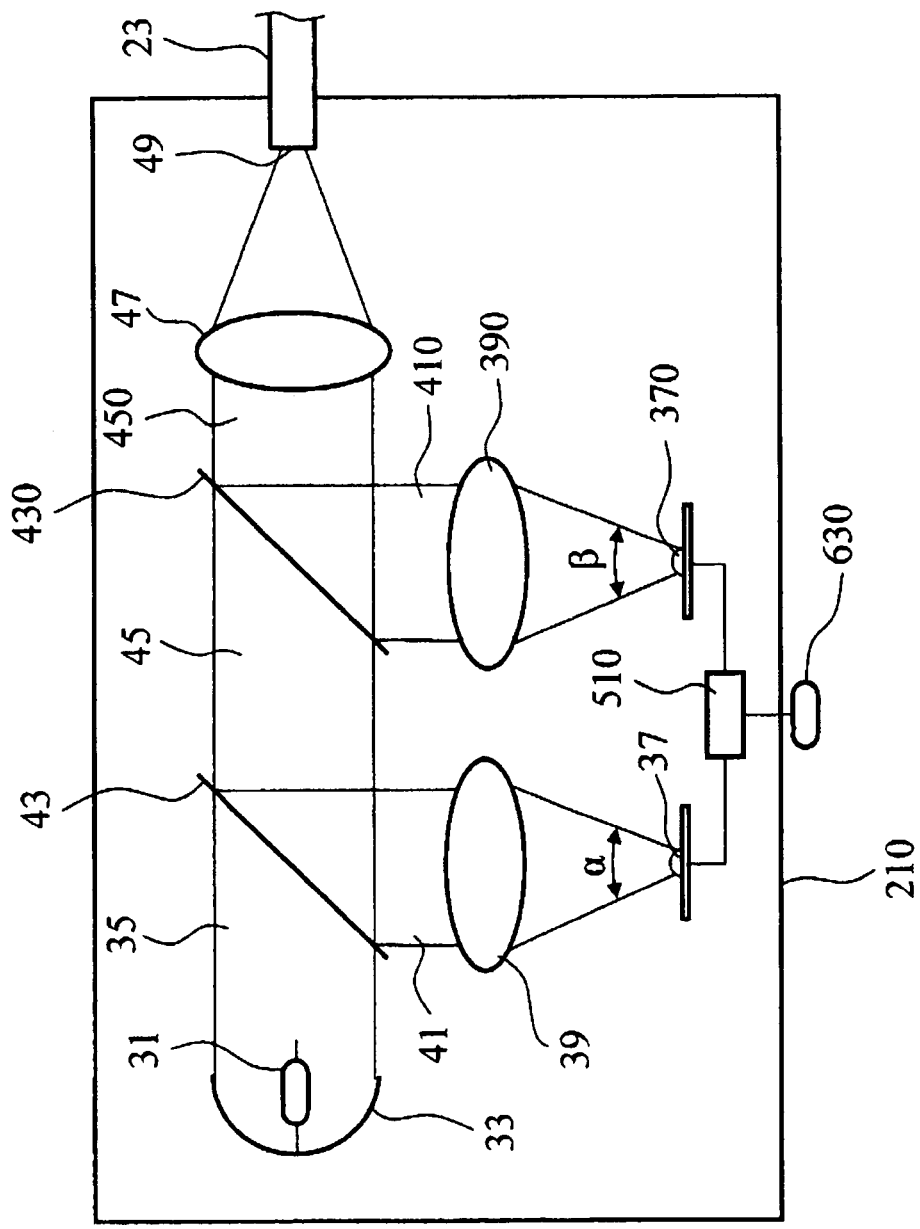

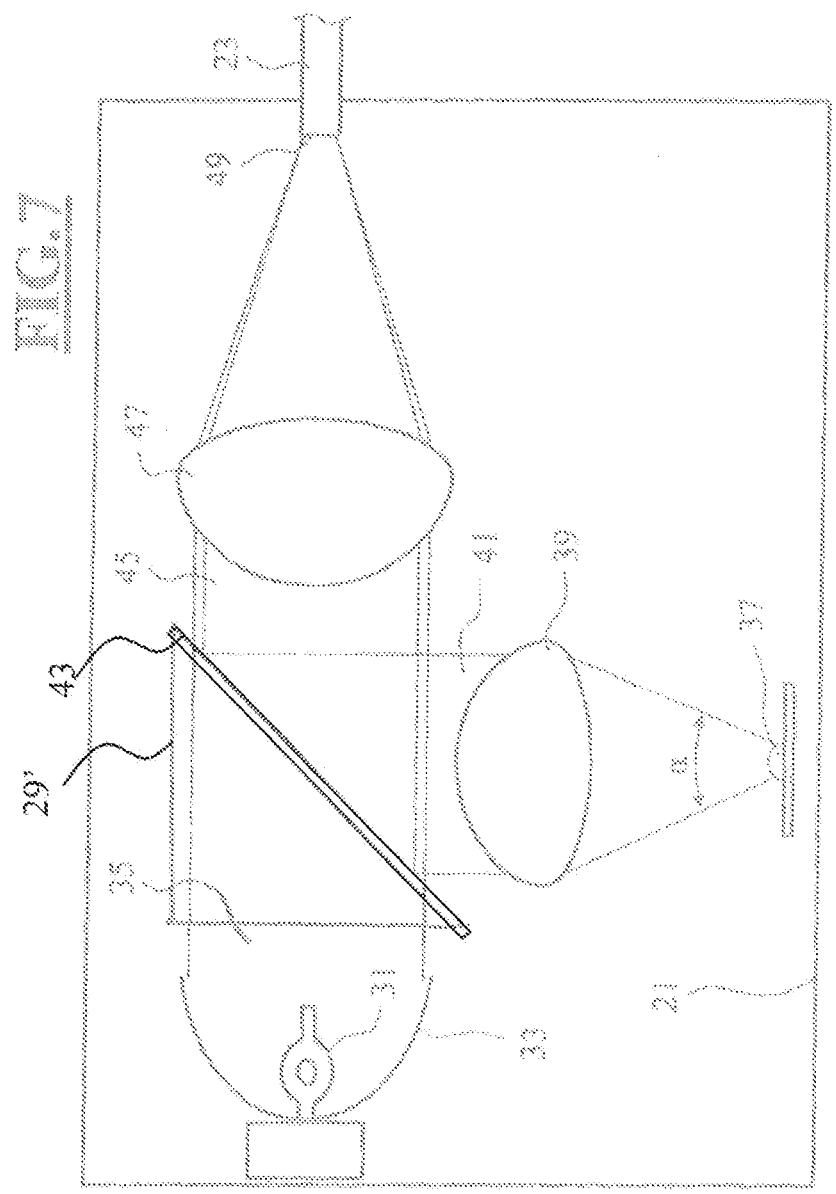

ILLUMINATING SYSTEM AND AN OPTICAL VIEWING APPARATUS INCORPORATING SAID ILLUMINATING SYSTEM

CROSS REFERENCE TO RELATED APPLICATION

This application claims priority of German patent application no. 10 2009 025 127.8, filed Jun. 17, 2009, the entire content of which is incorporated herein by reference.

FIELD OF THE INVENTION

The invention relates to an optical viewing apparatus as well as an illuminating system for an optical viewing apparatus which includes at least one broadband light source and a narrowband light source.

BACKGROUND OF THE INVENTION

Optical viewing apparatus such as surgical microscopes or endoscopes are often not provided only for conventional viewing of the viewed object but are also used, for example, to carry out a fluorescence measurement. For this purpose, the optical viewing apparatus includes a fluorescent light source which emits a wavelength suitable for exciting fluorescence in the viewed object. In conventional optical viewing apparatus, high power white light sources are often used, that is, broadband light sources which are driven at maximum power for fluorescence excitation. In this connection, over 99% of the electric power of the high power white light source is converted into heat which must be conducted away. In addition, the radiation intensity can, however, be too weak for weak fluorescence or deep surgical channels. Furthermore, the operation of a high power white light source at maximum power leads to a stress on the patients which, in turn, can lead to the situation that the fluorescence operation must be limited with respect to time. An endoscope having a white light source, which is used as a fluorescence light source, is described, for example, in U.S. Pat. No. 6,510,338.

In addition to the use of white light sources as excitation light sources for fluorescence, the use of light diodes or lasers as excitation light sources are also known.

A surgical microscope is described in United States patent publication 2006/0232855 wherein the fluorescence radiation is not generated with a white light source but with a semiconductor laser. This laser light is coupled into the illuminating beam path of the microscope below the main objective.

In published United States patent application 2005/0152029, a fluorescence microscope is described which includes an incandescent lamp for transmissive illumination of the object and a light diode as an excitation light source for fluorescence radiation. The light of the light emitting diode (LED) is coupled into the illuminating beam path above the main objective.

United States published patent application 2005/0224692 discloses a fluorescence microscope having a fluorescence light source based on several light emitting diodes.

German utility model registrations 20 2004 010 121 U1 and 20 2006 000 018 U1 describe the use of light emitting diodes as fluorescence light sources in microscopes.

SUMMARY OF THE INVENTION

It is an object of the invention to provide an advantageous illuminating system for an optical viewing apparatus which includes a white light illumination as well as a narrowband light source for exciting a fluorescence in the viewed object. It is another object of the invention to provide an advantageous optical viewing apparatus.

DETAILED DESCRIPTION OF THE INVENTION

An illuminating system of the invention for an optical viewing apparatus, which is operable in a fluorescence mode, includes at least one broadband light source for illuminating a viewed object, for example, a halogen lamp, a gas discharge lamp, a metal-halide lamp, a broadband semiconductor light source, a broadband organic light source, et cetera. In addition, the illuminating system includes at least one narrowband light source for exciting fluorescence in the viewed object and/or for background illumination in the fluorescence mode. The narrowband light source can be especially a laser or a luminescence emitter such as a light emitting diode or an organic light emitting diode, et cetera. Furthermore, the illuminating system of the invention includes a light conductor having a light source end inlet end and an object end outlet end as well as a superposer for superposing the light of the narrowband light source with the light of the broadband light source. The superposer can especially include at least one dichroic mirror and, for example, be configured as a prism 29' having at least one prism surface provided with a dichroic mirror 43, as depicted in FIG. 7. The superposer is mounted at the inlet end of the light conductor or, ahead of the inlet end of the conductor at the light source side. When the superposer is configured as a prism, it affords the advantage that light from more than two light sources can be superposed by the same superposer.

In the illuminating system of the invention, the white light as well as the excitation light for the fluorescence are conducted in common through the light conductor onto the object. In a surgical microscope, a light source of this kind can replace a conventional illuminating system with a light conductor through which the light is conducted to the optical viewing apparatus without changes in the construction of the optical viewing apparatus being necessary such as for coupling the excitation radiation into the viewing beam path. The illuminating system of the invention is therefore suitable in an advantageous manner also for retrofitting or refitting existing optical viewing apparatus to fluorescence apparatus.

In a further advantageous embodiment of the illuminating system of the invention, the illuminating system includes a switching unit for individually switching the narrowband light source on and off independently of the switched state of the broadband light source. In this configuration, the narrowband light source can be switched on and off independently of the broadband light source. For this reason, for example, the fluorescence can be excited with the broadband light source and the narrowband light source can be additionally applied as needed for exciting the fluorescence in order to increase the intensity of the excitation radiation relative to the sole use of the broadband light source. Especially for weak fluorescence, the generation of fluorescence radiation can thereby be brought about with adequate intensity. Even for deep surgical channels, it can be advantageous to increase the excitation intensity relative to the sole use of the broadband light source for exciting the fluorescence by switching in the narrowband light source. If, in addition, the broadband light can be switched on and off independently of the narrowband light source, then the narrowband light source can also be used by itself for fluorescence excitation, that is, without the broadband light source.

When the illuminating system includes an adjusting device for individually adjusting the intensity of the broadband light source independently of the intensity of the narrowband light source, then, during the fluorescence excitation, the broadband light source as a background illumination can be held to a low intensity level sufficient for the conventional viewing of the viewed object, that is, the broadband light source need not be operated at maximum power in order to make sufficient excitation radiation available. In this way, the stress on the patient because of the high white light intensity can be avoided during fluorescence excitation.

For example, if a separate adjustment of the intensity of the light sources and/or an individual switching on and off of the light sources is not possible, it is advantageous when the illuminating system has an attenuator and/or a filter which are introduced or which can be introduced between the broadband light source and the inlet end of the light conductor. The intensity of the broadband light source can be reduced by means of the attenuator and/or the filter during a fluorescence measurement wherein the illuminating system is supplied with maximum power. In the event that a filter is used, the filter is preferably transmissive for the wavelength of the narrowband light source. Preferably, the attenuator and/or the filter are mounted or can be introduced between the broadband light source and the superposer because, in this way, an influencing of the light of the narrowband light source does not occur. For this reason, there is also a greater degree of freedom in the selection of the material parameters for the attenuator and/or the filter with this positioning of the attenuator or filter.

In a further embodiment of the invention, the illuminating source includes at least two narrowband light sources whereby a higher intensity of the excitation radiation for the fluorescence can be achieved. If, in addition, a switching arrangement is provided for the individual switching on and off of the at least two narrowband light sources independently of each other, the intensity of the excitation radiation can be increased by switching in at least one of the narrowband light sources which is especially advantageous when there is weak fluorescence or deep surgical channels. If an adjusting device is present for individually adjusting the intensity of the at least two narrowband light sources independently of each other, the intensity, with which the viewed object is illuminated for excitation of the fluorescence radiation, can be continuously adjusted over a wide range especially when the two narrowband light sources can, in addition, also be switched on and off separately.

It is also possible to provide at least two narrowband light sources which emit at different wavelengths. In this way, the excitation of different fluorescent molecules is possible with the same illuminating system.

An optical viewing apparatus according to the invention is equipped with an illuminating system of the invention. An optical viewing apparatus of this kind has the features, characteristics and advantages described above with reference to the illuminating system.

The optical viewing apparatus can be realized especially as a surgical microscope or an endoscope.

BRIEF DESCRIPTION OF THE DRAWINGS

The invention will now be described with reference to the drawings wherein:

FIG. 7 is a schematic of a fifth embodiment of the illuminating system of the invention.

DESCRIPTION OF THE PREFERRED EMBODIMENTS OF THE INVENTION

Figure 1:
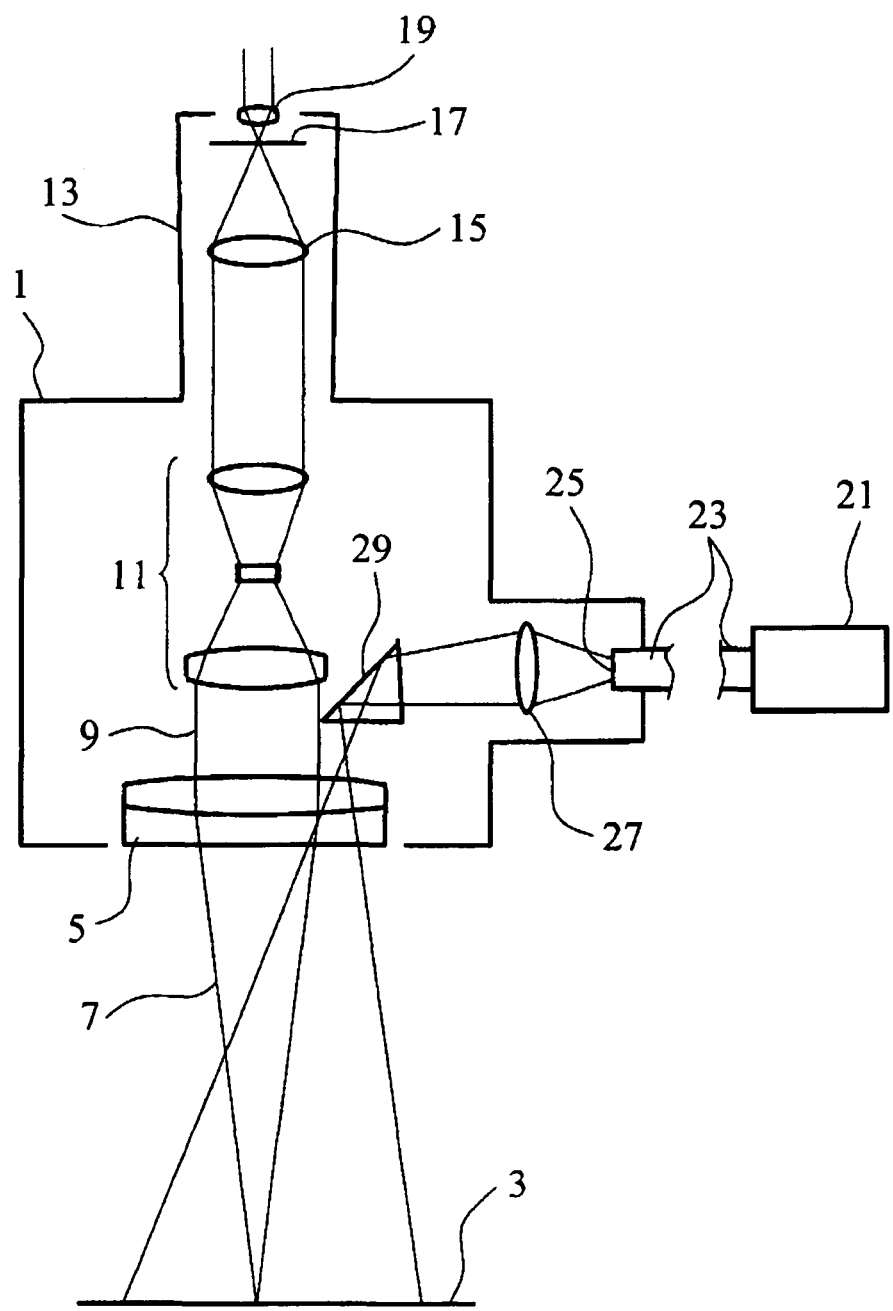
FIG. 1 is a schematic of a surgical microscope having an illuminating system according to the invention.

In the following, and with reference to FIG. 1, an example for the basic configuration of a surgical microscope having an illuminating system of the invention is described as an embodiment for an optical viewing apparatus of the invention. FIG. 1 shows the surgical microscope 1 in a side elevation view so that only one of the two stereoscopic component beam paths of the surgical microscope is shown.

The surgical microscope 1 includes an objective 5 which is to be directed toward the viewed object 3. In this embodiment, the objective 5 is shown as an achromatic lens or an apochromatic lens built up of two component lenses cemented to each other. The viewed object 3 is, for example, an area of tissue on which a fluorescence measurement is to be made. The viewed object 3 is arranged in the focal plane of the objective 5 so that the tissue region 3 is imaged at infinity. More specifically, a beam 7 of divergent rays emanating from the tissue region 3 is converted into a beam 9 of parallel rays when passing through the objective 5. In lieu of only an achromatic lens as it is used for objective 5 in the present embodiment, an objective lens system of several individual lenses can be used, for example, a so-called vario objective with which the work distance of the surgical microscope 1 can be varied, that is, the distance of the focal plane from the objective 5. In such a vario system too, the tissue region 3, which is disposed in the focal plane, is imaged to infinity so that, at the viewing end, a beam 9 of parallel rays is also present with a vario objective.

A magnification changer 11 is mounted at the viewing side of the objective 5 and this magnification changer can be configured either as a zoom system for continuously changing the magnification factor as shown in the embodiment or as a galilei changer for changing the magnification factor in a stepwise manner. A zoom system, as a rule, is configured of a lens combination having, for example, three or four lenses. In a zoom system, the two object end lenses can be displaced in order to vary the magnification factor. In a galilei changer, several fixed lens combinations are present which represent different magnification factors and they can be alternately introduced into the beam path. A zoom system as well as a galilei changer convert an object end beam of parallel rays into a beam of parallel rays at the viewer end having a different beam diameter. The magnification changer 11 is therefore already part of the binocular beam path of the surgical microscope 1, that is, the surgical microscope has its own lens combination for each stereoscopic component beam path of the surgical microscope 1. Alternatively, the magnification changer can, however, also be configured as a large optic, that is, with lenses through which both stereoscopic component beam paths pass. An interface can be disposed on the magnification changer 11 at the viewer end. At this interface, external apparatus can be connected to the surgical microscope 1 and this external apparatus can function, for example, to couple out part of the beam path from the surgical microscope and/or to mirror in data or other information.

In the surgical microscope 1, at the viewer end, a binocular tube 13 follows the magnification changer 11 or, if present, the interface. The binocular tube 13 includes two tube objectives 15 which focus the corresponding beam 9 of parallel rays into an intermediate plane 17, that is, the viewed object 3 is imaged onto the corresponding intermediate image plane 17. The intermediate images, which are disposed in the intermediate image plane 17, are, in turn, imaged at infinity by the oculars 19 so that a viewer can view the intermediate images with relaxed eyes. The viewer can, for example, be the treating physician or an assistant of the treating physician. Moreover, an expansion of the distance between the two stereoscopic component beams takes place in the binocular tube by means of a mirror system or by prisms (not shown) in order to adapt the distance to the interpupillary distance of the viewer.

The surgical microscope 1 of the invention shown in FIG. 1 further includes an illuminating system 21 mounted remote from the actual microscope body. The viewed object 3 is illuminated by the illuminating system 21 and the illuminating system 21 can excite a fluorescence of the tissue region 3, for example, because of a fluorescence coloring added to the tissue region 3. The fluorescence coloring can be indocyanine green or 5 aminolevulinic acid (5-ALA) or the like. The light, which is generated in the illuminating system 21, is coupled into the inlet end (not shown in FIG. 1) of a light conductor 23 and is conducted via the light conductor 23 to the microscope body wherein the outlet end 25 of the light conductor 23 is located. With a condenser system 27 arranged in the microscope body, a diaphragm, which is illuminated by the outlet end 25 of the light conductor 23, a diaphragm plane or some other plane is imaged via a deflection prism 29 onto the tissue region 3. Also, a path-folding mirror can basically be used here in lieu of a deflecting prism 29.

The illuminating system 21 is described hereinafter in greater detail with reference to FIGS. 2 to 6.

Figure 2:
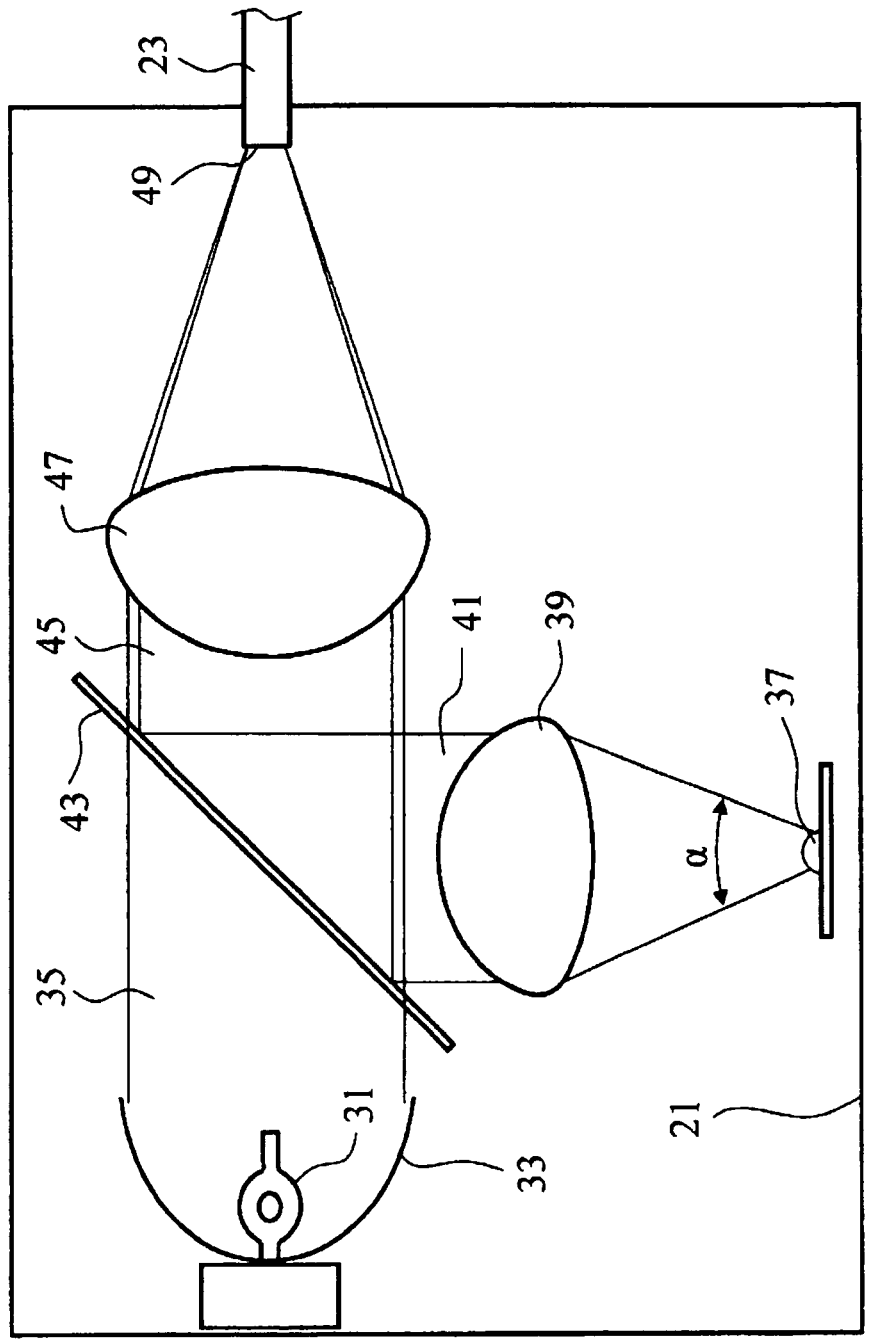
FIG. 2 shows a first embodiment of the illuminating system of the invention.

The illuminating system 21 of the invention is shown in detail in FIG. 2. The illuminating system 21 includes a white light source 31 in the form of a xenon high pressure lamp which functions as a broadband light source. The light emitted by the white light source 31 is collimated by a reflector 33 so that a beam 35 of parallel white light rays results. In lieu of the high pressure lamp, another white light source can be used to make available the broadband light, for example, a metal halide lamp, a halogen lamp, et cetera. Besides the abovementioned thermal radiators, also non-thermal radiators can be used such as lasers, light emitting diodes, organic light emitting diodes, et cetera. These non-thermal radiators can be used insofar as they are suitable for the emission of broadband light which can, for example, be achieved in the case of light emitting diodes via suitable converter coatings.

In the present embodiment, the illuminating system 21 further includes a light emitting diode 37 as a narrowband light source. The narrowband light, which is emitted by the light emitting diode 37 in a spatial angle range α, is collimated by a collimator lens 39 in order to generate a parallel ray beam 41 of narrowband illuminating light. The wavelength of the narrowband illuminating light is so selected that it can, in the observed tissue region 3 (see FIG. 1), cause a fluorescence, for example, of a suitable fluorescent coloring such as indocyanine green. In lieu of the described light emitting diode 37, also another luminescence radiator can be used, for example, an organic light emitting diode (OLED) or an electroluminescence foil.

In the illuminating system 21, there is, moreover, a partially transmissive mirror 43 which functions as a beam splitter and is so mounted that it permits a beam 35 of parallel white rays to pass and the parallel ray beam 41 of narrowband light is deflected in such a manner that it is superposed on the parallel ray white light beam 35 in order to generate a common parallel ray beam 45. The beam splitter can therefore be seen as a superposer. In lieu of the partially transmitting mirror 43, also other beam splitters such as a beam splitter prism can be used as superposers.

The parallel ray beam 45 of superposed light is focused onto the inlet end 49 of the light conductor 23 by a focusing lens 47 in order to in couple the superposed light into the light conductor 23. The inlet end 49 of the light conductor 23 is disposed in the illuminating system 21. The light exiting from the outlet end 25 of the light conductor 23 illuminates the tissue region 3 and contains, on the one hand, the white light as an illuminating light for optical viewing of the tissue region and, on the other hand, the narrowband light as excitation light for exciting a fluorescence in the tissue region 3.

The white light for optical viewing of the tissue region 3 and the excitation light for exciting a fluorescence are conducted through the same light conductor 23 to the main body of the surgical microscope 1. For this reason, there is no additional illuminating beam path necessary in the main body itself for the excitation light. Furthermore, an existing surgical microscope to which viewing light is supplied via a light conductor can be retrofitted with the aid of the illuminating system 21 of the invention in such a manner that a fluorescence viewing is possible. In addition, the illuminating system 21 of the invention permits supplying excitation light without it being necessary to provide additional structural space in the main body of the microscope.

Figure 3:
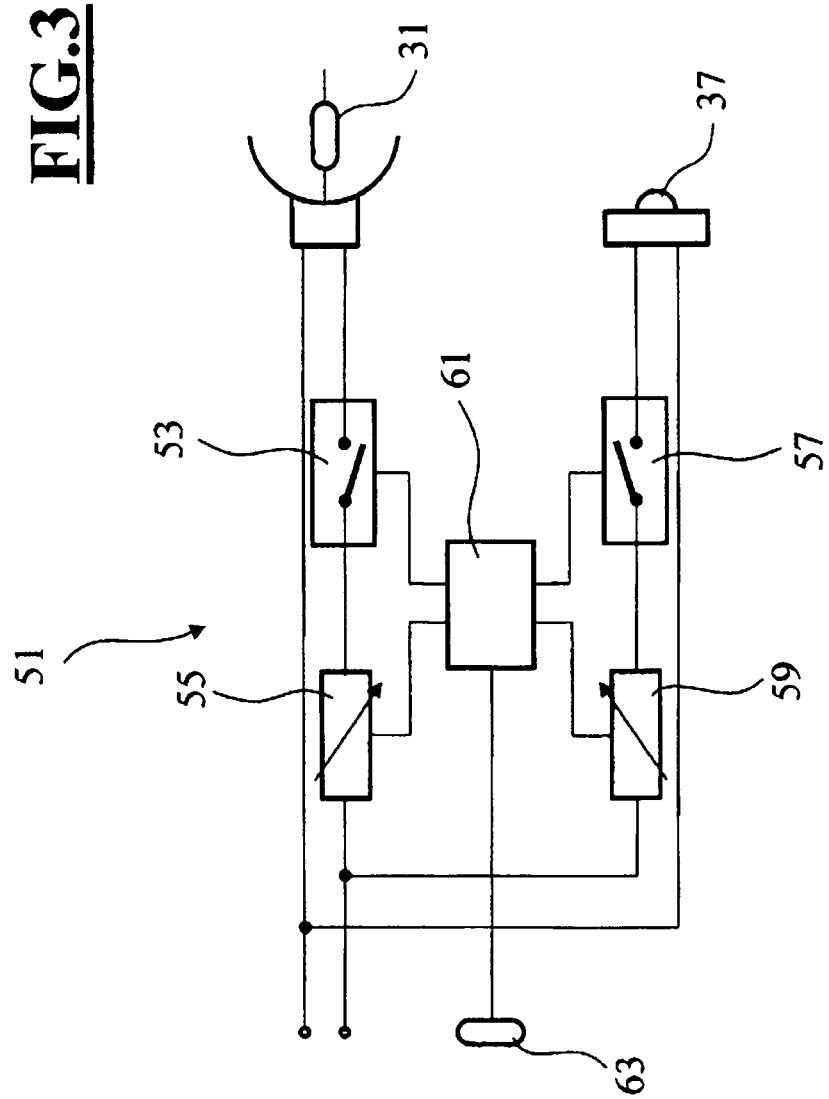
FIG. 3 is a schematic of a control circuit for the illuminating system of the invention.

The schematic of FIG. 3 shows an example of a control unit 51 with the aid of which the white light source 31 and the light emitting diode 37 can be individually switched on and switched off and which makes possible an individual adjustment of the light intensity of the particular light source. The control unit 51 includes a first controllable switch 53 and a first controllable potentiometer 55. The switch 53 and potentiometer 55 are assigned to supply current for the xenon high pressure lamp 31. Furthermore, the switching and control unit 51 includes a second controllable switch 57 as well as a second controllable potentiometer 59 which are assigned to the current supply for the light emitting diode 37. The adjustment of the resistance values at the potentiometers (55, 59) as well as the switching on and switching off of the switches (53, 57) is assumed by a central control unit 61 to which the values and switching states, which are to be adjusted, are supplied from an external source via an interface 63.

The circuit shown in FIG. 3 is only representative for many possible circuits which make it possible to switch on and off the light emitting diode 37 and the xenon lamp 31 independently from each other. Furthermore, the light intensities of the two light sources can be controlled individually. In this way, it is, on the one hand, possible, for example, to completely switch off the excitation illumination when it is not needed or to reduce the intensity of the white light illumination when a fluorescence viewing should take place.

It is again noted that the switches (53, 57) and potentiometers (55, 59) shown in FIG. 3 are only representative for functional units which, on the one hand, permit each light source to be switched on and off and which permit the intensity of the particular light source to be adjusted. Accordingly, it is, for example, also possible with light emitting diodes to adjust the light intensity utilizing pulse width modulation in lieu of constant current regulation. In lieu of potentiometer 59, the circuit 51 would then be equipped with a pulse width modulation unit assigned to the light emitting diode 37. Methods and functional units for adjusting the intensities of the white light source and the light emitting diodes are known to persons of ordinary skill and are therefore not further discussed here.

Figure 4:
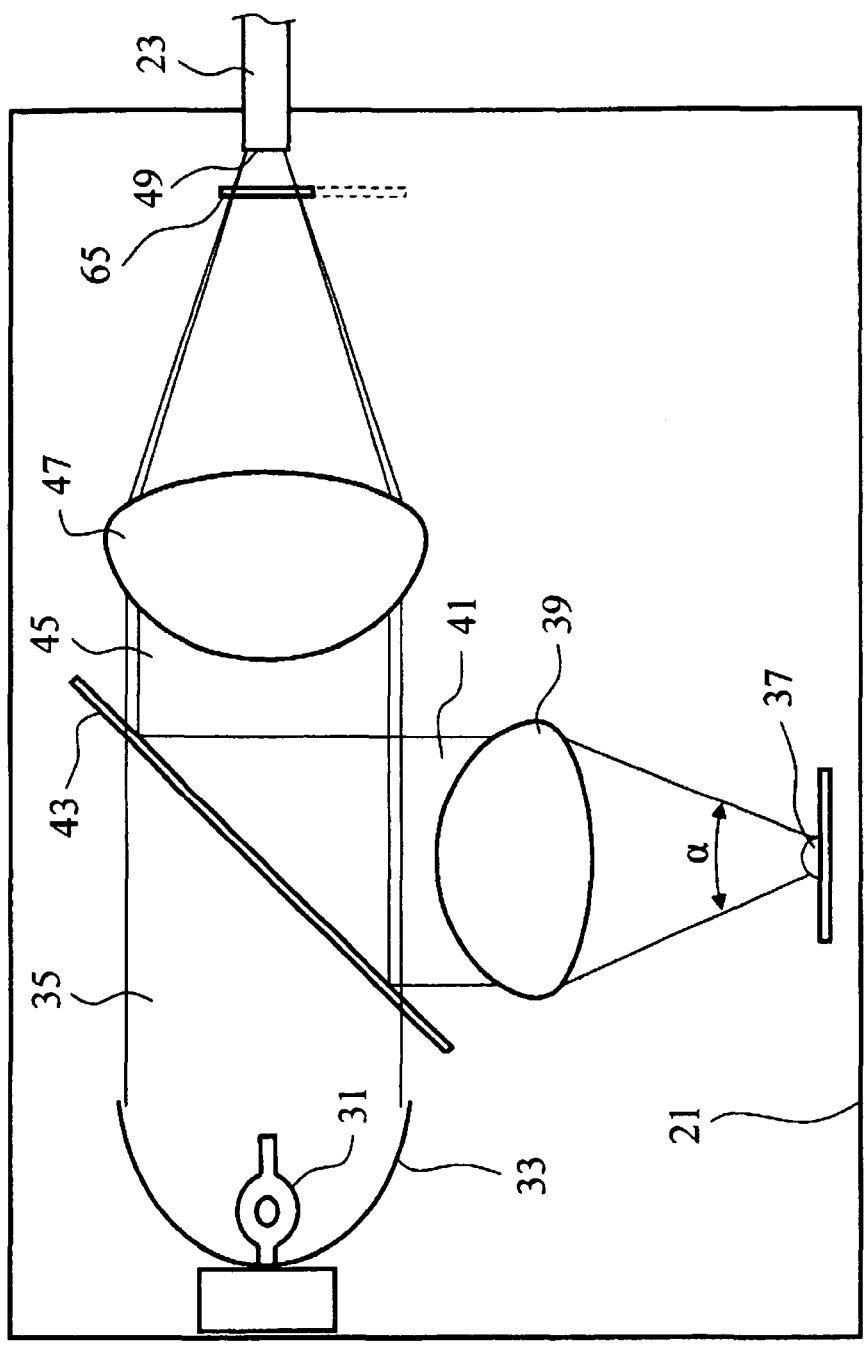
FIG. 4 is a schematic of a second embodiment of the illuminating system of the invention.

A second embodiment of the illuminating system 21 of the invention is shown in FIG. 4. Elements which correspond to those elements of the first embodiment are identified in FIG. 4 with the same reference numerals used in FIG. 2 and are therefore not described further hereinafter.

The second embodiment shown in FIG. 4 for the illuminating system 21 of the invention differs from the first embodiment in that a filter 65 is provided between the focusing lens 47 and the inlet end 49 of the light conductor 23. The filter 65 can be inserted into the beam path between the focusing lens 47 and the inlet end 49 of the light conductor 23. The filter 65 is shown in phantom outline for the position when not inserted into the beam path. The filter 65 can be pivoted into the beam path in lieu of being inserted as shown in FIG. 4. As filters 65, especially heat absorbing filters which filter out an infrared component of the light or color filters for increasing contrast such as yellow filters are considered.

In lieu of at the position shown in FIG. 4, the filter 65 can also be mounted at other positions of the beam path, for example, between the xenon lamp 31 and the beam splitter 43 or between the beam splitter 43 and the focusing lens 47. The location of the filter 65 shown in FIG. 4 affords, however, the advantage that the filter size can be minimized whereby the structural space needed for the filter in the illuminating system 21 can be held to a minimum. It is understood that in lieu of only one filter 65, more filters can be present which can be arranged either in the same section of the beam path, that is, all between the focusing lens 47 and the inlet end 49 of the light conductor 23 or in different sections of the beam path, for example, one filter between the focusing lens 47 and the inlet end 49 of the light conductor 23 and another filter between the xenon high pressure lamp 31 and the beam splitter 43.

Figure 5:
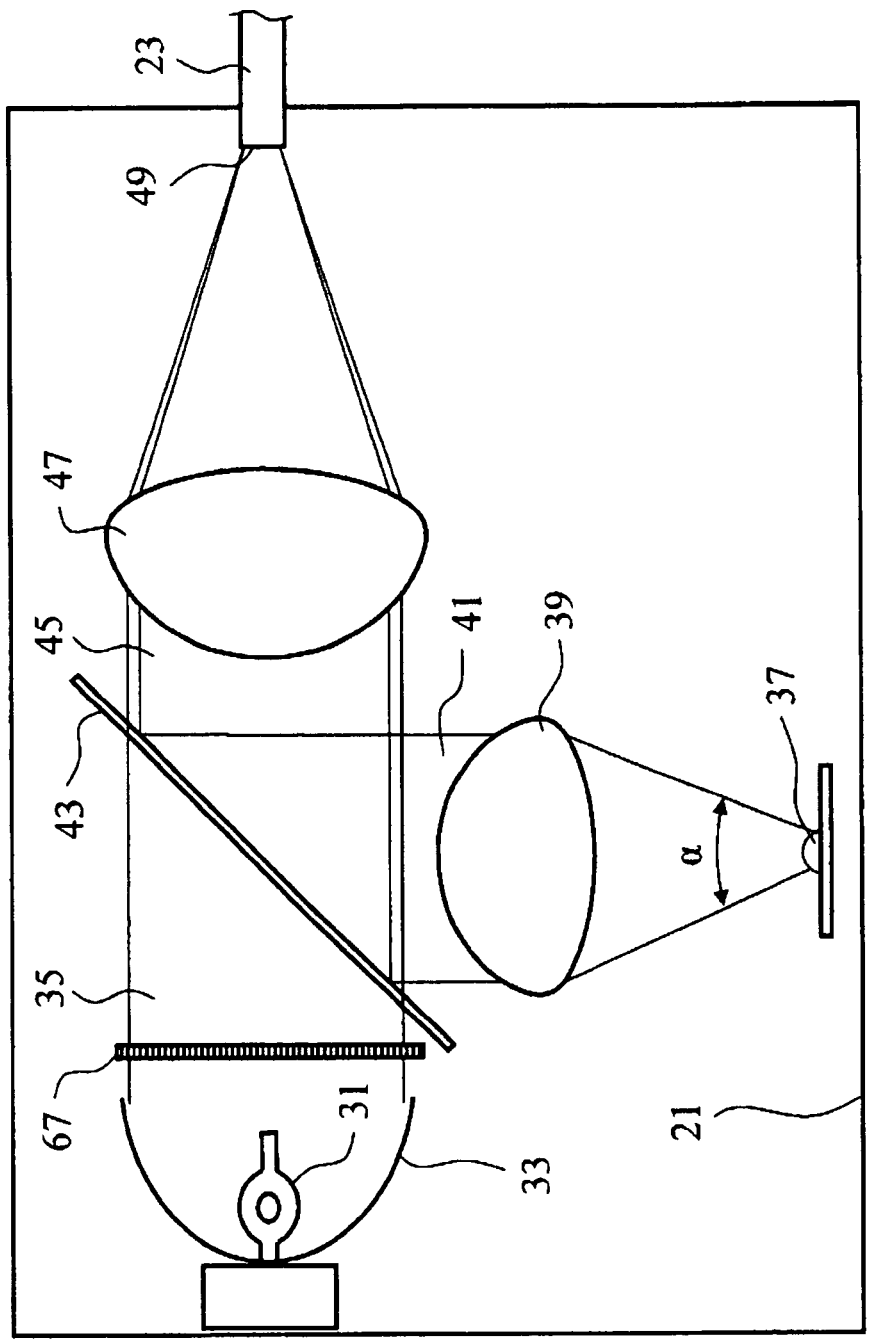
FIG. 5 is a schematic of a third embodiment of the illuminating system of the invention; and, FIG. 6 is a schematic of a fourth embodiment of the illuminating system of the invention.

A further embodiment of the illuminating system 21 of the invention is shown in FIG. 5. Those elements of the third embodiment, which correspond to the elements of the first embodiment, are identified with the same reference numerals as in FIG. 2 and are not further explained hereinafter.

The embodiment for the illuminating system 21 shown in FIG. 5 differs from the embodiment shown in FIG. 2 in that an attenuator 67 is mounted between the xenon high pressure lamp 31 and the beam splitter 43 in order to limit the intensity of the broadband illuminating light or to limit the maximum intensity of the broadband illuminating light when the light intensity of the white light source is adjustable. In the present embodiment, the attenuator 67 is configured as a sieve diaphragm, that is, a diaphragm having a plurality of apertures formed therein. Basically, the attenuator can, however, also be realized with other components, for example, by transmission displays, polarizers or other optical components having changeable transmission or reflection.

A fourth embodiment for the illuminating system 21 of the invention is shown in FIG. 6. Elements which correspond to those of the illuminating system of the first embodiment shown in FIG. 2 are identified by the same reference numerals as in FIG. 2 and are not further discussed hereinafter.

The fourth embodiment for the illuminating system 210 of the invention shown in FIG. 6 differs from the previously described embodiments in that a second narrowband light source 370 is provided having light which differs in its wavelength from the light of the first narrowband light source 37. For the type of light source used, the explanation of the first narrowband light source 37 applies. In the present embodiment, the second narrowband light source 370 is a light emitting diode like the first narrowband light source 37.

The narrowband light emitted by the light emitting diode 370 is emitted in the spatial angle range $\beta$. This light is converted by a collimator lens 390 into a parallel ray beam of narrowband light 410. A second beam splitter 430 can be configured like the first beam splitter 43, especially as a partially transmissive mirror or be configured as a prism. The narrowband light of the second light source 370 is superposed by means of the second beam splitter 430 onto the parallel ray beam 45 which contains the light of the white light source superposed with the light of the first narrowband light source 37. For this purpose, the beam splitter 430 allows the parallel ray beam 45 of superposed light of the white light source and the first narrowband light source 37 to pass without deflection whereas the beam splitter 430 deflects the parallel ray beam 410 with the narrowband light of the second narrowband light source 370 in order to generate an illuminating beam having all three illuminating light components 450 which then is imaged on the inlet end 49 of the light conductor 23 by the focusing lens 47.

The fourth embodiment further includes a switching and adjusting module 510 with which the narrowband light sources (37, 370) can be switched on and off separately from each other. Furthermore, the switching and adjusting module 510 is so configured that it permits an individual control of the light intensity of the narrowband light sources (37, 370). For this purpose, the switching and adjusting module 510 can include a pulse width modulation unit for each narrowband light source (37, 370). The states which can be set by the switching and adjusting module 510 can be supplied externally via the interface 630.

In the fourth embodiment, a filter can also be used as has been described with respect to the second embodiment or, an attenuator can be used as described with reference to the third embodiment.

The described embodiments set forth only possibilities as to how the illuminating system of the invention can be realized. Deviations from these embodiments are possible. For example, the illuminating system can have an attenuator as described in the third embodiment as well as one or more filters as described in the second embodiment. The number of narrowband and broadband light sources is basically not limited. Especially, a plurality of narrowband light sources can be used which emit at different wavelengths for exciting the fluorescence of different fluorescing molecules.

It is understood that the foregoing description is that of the preferred embodiments of the invention and that various changes and modifications may be made thereto without departing from the spirit and scope of the invention as defined in the appended claims.

What is claimed is:

1. A surgical microscope for viewing an object in a form of tissue, the surgical microscope comprising:
   a body having a viewing end;
   an ocular mounted in said body at said viewing end;
   an objective mounted in said body between said ocular and the object;
   said ocular and said objective conjointly defining a viewing beam path to said object;
   an illuminating system operable in a fluorescence mode;
   said illuminating system including a broadband light source for illuminating an object to be viewed; said broadband light source having an intensity and defining a beam path and emitting a white light beam travelling along said beam path and illuminating said object; a narrowband light source defined by an electroluminescence radiator having a wavelength and being configured for exciting fluorescence of fluorescing molecules in said object; a light conductor having an inlet end facing toward said light sources; a superposer mounted in said beam path for superposing light of said electroluminescence radiator onto said white light beam of said broadband light source to form a composite light beam; said superposer including a prism having a surface provided with a dichroic mirror and being mounted at or ahead of said inlet end of said light conductor; an attenuator mounted in said beam path between said broadband light source and said superposer and having at least one of a changeable transmission and a changeable reflection; and, a filter inserted or insertable into said beam path between said superposer and said inlet end of said light conductor;

a first control unit for individually switching said electroluminescence radiator on and off independently of a switching state of said broadband light source;

a second control unit for individually adjusting the intensity of said broadband light source independently of an intensity of said electroluminescence radiator;

said light conductor extending into said body of said microscope and having an outlet end wherefrom said composite light beam passes;

a condenser system being arranged in said body of said microscope downstream of said outlet end;

a path-folding device for receiving said composite light beam from said condenser system and directing said composite light beam toward said objective and said object;

a focusing lens disposed between said superposer and said filter; and, said filter being transmissive for the wavelength of said electroluminescence radiator.

2. The surgical microscope of claim 1, wherein said narrowband light source is a first narrowband light source; and, wherein said illuminating system further comprises a second narrowband light source.

3. The surgical microscope of claim 2, further comprising a circuit for individually switching said first and second narrowband light sources on and off independently of each other.

4. The surgical microscope of claim 3, wherein said circuit further comprises an adjusting device for individually adjusting an intensity of said first and second narrowband light sources independently of each other.

5. The surgical microscope of claim 2, wherein said first and second narrowband light sources emit at different wavelengths.

6. A surgical microscope for viewing an object in a form of tissue, the surgical microscope comprising:

a body having a viewing end;

an ocular mounted in said body at said viewing end;

an objective mounted in said body between said ocular and the object;

said ocular and said objective conjointly defining a viewing beam path to said object;

an illuminating system operable in a fluorescence mode;

said illuminating system including a broadband light source for illuminating an object to be viewed; said broadband light source defining a beam path and emitting a white light beam travelling along said beam path and illuminating said object; a first narrowband light source having an intensity and being provided for emitting light at a first wavelength for exciting first fluorescence molecules in said object; a second narrowband light source having an intensity and being provided for emitting light at a second wavelength different from said first wavelength for exciting second fluorescence molecules in said object different from said first fluorescence molecules; a light conductor having an inlet end facing toward said light sources; a first superposer mounted in said beam path for superposing the light of said first narrowband light source onto said white light beam; and, a second superposer mounted in said beam path downstream of said first superposer for superposing the light of said second narrowband light source onto said white light beam and the light of said first narrowband light source to form a composite light beam;

a first control unit for individually adjusting the intensities of said first and second narrowband light sources independently of each other;

a second control unit for individually adjusting the intensity of said broadband light source independently of the intensities of said first and second narrowband light sources;

said light conductor extending into said body of said surgical microscope and having an outlet end wherefrom said composite light beam passes;

a condenser system being arranged in said body of said surgical microscope downstream of said outlet end;

a path-folding device for receiving said composite light beam from said condenser system and directing said composite light beam toward said objective and said object;

a focusing lens disposed between said second superposer and said inlet end of said light conductor; and, a filter inserted or insertable between said focusing lens and said inlet end of said light conductor.

7. The surgical microscope of claim 6, wherein each of said superposers comprises a prism having a surface provided with a dichroic mirror.

8. The surgical microscope of claim 7, wherein each of said narrowband light sources is an electroluminescence radiator.

9. The surgical microscope of claim 6, wherein each of said narrowband light sources is an electroluminescence radiator.

10. The surgical microscope of claim 6, wherein said first narrowband light source is arranged so as to be in spaced relationship from said second narrowband light source.

11. An endoscope for viewing an object in a form of tissue, the endoscope comprising:

a body having a viewing end;

an ocular mounted in said body at said viewing end;

an objective mounted in said body between said ocular and the object;

said ocular and said objective conjointly defining a viewing beam path to said object;

an illuminating system operable in a fluorescence mode;

said illuminating system including a broadband light source for illuminating an object to be viewed; said broadband light source having an intensity and defining a beam path and emitting a white light beam travelling along said beam path and illuminating said object; a narrowband light source defined by an electroluminescence radiator having a wavelength and being provided for exciting fluorescence of fluorescing molecules in said object; a light conductor having an inlet end facing toward said light sources; a superposer mounted in said beam path for superposing light of said electroluminescence radiator onto said white light beam of said broadband light source to form a composite light beam; said superposer including a prism having a surface provided with a dichroic mirror and being mounted at or ahead of said inlet end of said light conductor; an attenuator mounted in said beam path between said broadband light source and said superposer and having at least one of a changeable transmission and a changeable reflection; and, a filter inserted or insertable into said beam path between said superposer and said inlet end of said light conductor;

a first control unit for individually switching said electroluminescence radiator on and off independently of a switching state of said broadband light source;

a second control unit for individually adjusting the intensity of said broadband light source independently of an intensity of said electroluminescence radiator;

said light conductor extending into said body of said endoscope and having an outlet end wherefrom said composite light beam passes;

a condenser system being arranged in said body of said endoscope downstream of said outlet end;

a path-folding device for receiving said composite light beam from said condenser system and directing said composite light beam toward said objective and said object;

a focusing lens disposed between said superposer and said filter; and, said filter being transmissive for the wavelength of said electroluminescence radiator.

* * * * *